United States Patent [19]
Vaeck et al.

[11] Patent Number: 5,516,693
[45] Date of Patent: May 14, 1996

[54] HYBRID GENE INCORPORATING A DNA FRAGMENT CONTAINING A GENE CODING FOR AN INSECTICIDAL PROTEIN, PLASMIDS, TRANSFORMED CYANOBACTERIA EXPRESSING SUCH PROTEIN AND METHOD FOR USE AS A BIOCONTROL AGENT

[75] Inventors: Mark A. Vaeck, Aarschotse Baan; Wipa Chungjatupornchai, Kortrijuse Steenweg, both of Belgium; Lee McIntosh, East Lansing, Mich.

[73] Assignee: Board of Trustees operating Michigan State University, East Lansing, Mich.

[21] Appl. No.: 21,405

[22] Filed: Mar. 4, 1987

[51] Int. Cl.$^6$ ............................ C12N 15/70; C12N 15/32
[52] U.S. Cl. .................. 435/320.1; 435/69.7; 435/172.3; 435/252.33; 536/23.4; 536/23.71
[58] Field of Search .................. 435/68, 91, 170, 435/172.3, 258, 320, 822, 832, 320.1, 69.7; 935/1, 6, 8, 9, 22, 23, 29, 38, 41, 59, 60, 63, 64, 72, 73, 74; 424/93; 536/23.4, 23.71

[56] References Cited

U.S. PATENT DOCUMENTS 4,695,455  9/1989  Barnes et al. ........................... 424/93.2

OTHER PUBLICATIONS

Dzelzkalns et al 1984 *NAR* 12:8917–25.
Sekar, V. 1986, *Biochem Biophys Res. Comm.* 137: 748–751.
Sekar et al. 1985. *Gene* 33:151–58.
Ganesan et al. 1983 *MGG* 189:181–183.
Nierzwicki–Bauer et al. 1983. *PNAS* 80:1835–39.
Nierzwicki–Bauer et al 1984. *PNAS* 81:5961–65.
Chaurat et al. 1986 *MGG* 204: 185–91.
Reiss et al. 1984 *EMBO J* 3(13):3317–22.
Kolowsky et al. 1984. *Gene* 27:289–299.
Miller et al. 1979. *J Bacteriol* 140:246–50.
ATCC Catalogue of Bacteria & Bacteriophages, 17th Ed., 1989. pp. 248–249.
Brock, T. D. 1979. Biology of Microorganisms. Prentice–Hall, N.J. pp. 627 and 629.
Bold et al. 1985. Introduction to the Algae: Structure and reproduction. Prentice–Hall, N.J. pp. 34–35, 38–39 & 47–51.
Goldberg et al., Mosquito News 37; 355–358 (1977).
Thomas et al., J. Cell Sci., 60; 181–197 (1983).
Yamamoto et al., Curr. Microbiol. 9; 279–284 (1983).
Armstrong et al., J. Bacteriol. 161; 39–46 (1985). *mistype in application as 1984.
Ward et al., FEBS 175; pp. 377–382 (1984).
Visser et al., FEMS Microbiol. Lett., 30; 211–214 (1986).
McIntosh et al., In Molecular Form and Function of the Plant Genome, Plenum Press, New York, pp. 335–346 (1985).
Shestakov et al., Mol. Gen. Genet., 107; 372–375 (1970).
Stevens et al., PNAS, USA, 77; 6052–6056 (1980).
Griogoreiva et al., FEMS Microbiol. Lett. 13; 367–370 (1982).
Buzby et al., J. Bacteriol. 154; 1446–1450 (1983).
Van den Hondel et al., PNAS, USA, 77; 1570–1574 (1980).
Wolk et al., PNAS, USA, 81; 1561–1565 (1984).
Ruvkun et al., Nature, 289; 85–88 (1981).
Tanenau de Marsac et al., Gene, 20; 111–119 (1982).
Williams et al., Gene 24; 37–51 (1983).
Reiss et al., Embo J., e; 3317 (1984).
Maniatis et al., In Molecular Cloning, A Laboratory Manual, Cold Spring Harbor Lab., New York, (1982). pp. 109–112.
Rippka et al., J. Gene. Microbiol. III; 1–61, (1979).
Bolivar et al., Methods Enzymol. 68;245–267, (1979).
Friedberg et al., Mol. Gen. Genet. 203; 505–510, (1986).
Curtis et al., PNAS, 80; 1835–1839 (1983).
Nierzwicki–Bauer et al., PNAS, 81; 5961–5965 (1984).
Bulla et al., J. Bacteriol., 130; pp. 375–383, (1977).

*Primary Examiner*—John L. LaGuyader
*Attorney, Agent, or Firm*—Ian C. McLeod

[57] ABSTRACT

The instant invention is drawn to plasmid p1BN10 harbored in *E. coli* DSM 4020 and coding for a *Bacillus thuringiensis* endotoxin (Bt8 toxin) fused in frame to the neo gene of pBR322.

1 Claim, 13 Drawing Sheets

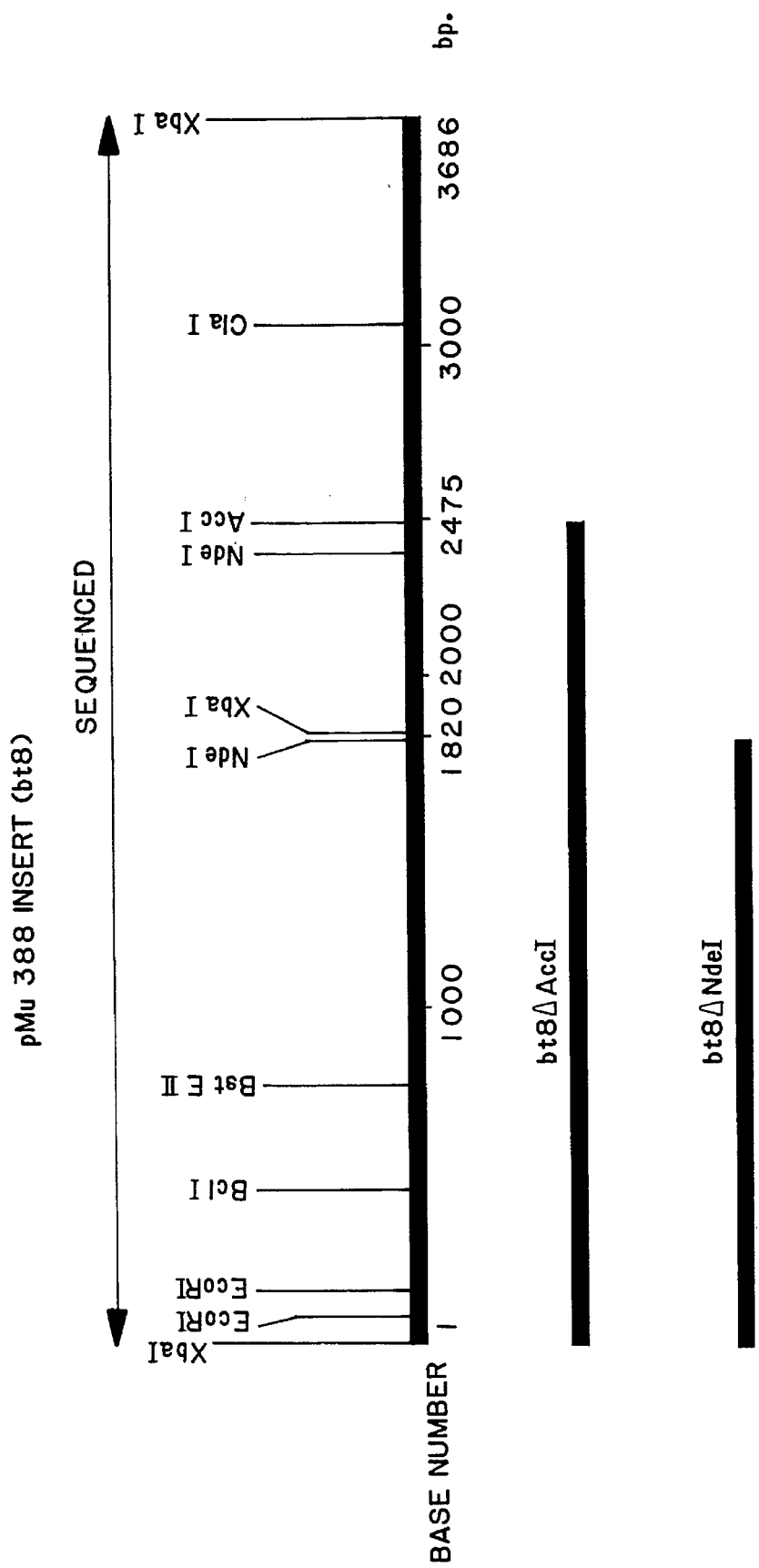

FIG. 2a-1

```
         10        20        30        40        50        60
GATAAGAATTGTTCATAGGAATCCGTATCAATTTTTTCAAGGAATATGTATTTGCACTTT
         70        80        90       100       110       120
TGGTCTTTTTAAATCGTATGAATTCAAAATAGTTTATATCAATCTTTGTTACACCAGAAA
        130       140       150       160       170       180
AAGATTGTATCCAATGTGAATATGGGAGGAATAAATATGAATTCAGGCTATCCGTTAGCG
                                       MetAsnSerGlyTyrProLeuAla
        190       200       210       220       230       240
AATGACTTACAAGGGTCAATGAAAAACACGAACTATAAAGATTGGCTAGCCATGTGTGAA
AsnAspLeuGlnGlySerMetLysAsnThrAsnTyrLysAspTrpLeuAlaMetCysGlu
        250       260       270       280       290       300
AATAACCAACAGTATGGCGTAATCCAGCTGCGATTAATTCTTCTTCAGTTAGTACCGCT
AsnAsnGlnGlnTyrGlyValAsnProAlaAlaIleAsnSerSerSerValSerThrAla
        310       320       330       340       350       360
TTAAAAGTAGCTGGAGCTATCCTTAAATTTGTAAACCCACCTGCAGGTACTGTCTTAACC
LeuLysValAlaGlyAlaIleLeuLysPheValAsnProProAlaGlyThrValLeuThr
        370       380       390       400       410       420
GTACTTAGCGCGGTGCTTCCTATTCTTTGGCCGACTAATACTCCAACGCCTGAAAGAGTT
ValLeuSerAlaValLeuProIleLeuTrpProThrAsnThrProThrProGluArgVal
        430       440       450       460       470       480
TGGAATGATTTCATGACCAATACAGGGAATCTTATTGATCAAACTGTAACAGCTTATGTA
TrpAsnAspPheMetThrAsnThrGlyAsnLeuIleAspGlnThrValThrAlaTyrVal
        490       500       510       520       530       540
CGAACAGATGCAAATGCAAAAATGACGGTTGTGAAAGATTATTTAGATCAATATACAACT
ArgThrAspAlaAsnAlaLysMetThrValValLysAspTyrLeuAspGlnTyrThrThr
        550       560       570       580       590       600
AAATTTAACACTTGGAAAAGAGAGCCTAATAACCAGTCCTATAGAACAGCAGTAATAACT
LysPheAsnThrTrpLysArgGluProAsnAsnGlnSerTyrArgThrAlaValIleThr
        610       620       630       640       650       660
CAATTTAACTTAACCAGTGCCAAACTTCGAGAGACCGCAGTTTATTTTAGCAACTTAGTA
GlnPheAsnLeuThrSerAlaLysLeuArgGluThrAlaValTyrPheSerAsnLeuVal
        670       680       690       700       710       720
GGTTATGAATTATTGTTATTACCAATATACGCACAAGTAGCAAATTTCAATTTACTTTTA
GlyTyrGluLeuLeuLeuLeuProIleTyrAlaGlnValAlaAsnPheAsnLeuLeuLeu
        730       740       750       760       770       780
ATAAGAGATGGCCTCATAAATGCACAAGAATGGTCTTTAGCACGTAGTGCTGGTGACCAA
IleArgAspGlyLeuIleAsnAlaGlnGluTrpSerLeuAlaArgSerAlaGlyAspGln
        790       800       810       820       830       840
CTATATAACACTATGGTGCAGTACACTAAAGAATATATTGCACATAGCATTACATGGTAT
LeuTyrAsnThrMetValGlnTyrThrLysGluTyrIleAlaHisSerIleThrTrpTyr
        850       860       870       880       890       900
AATAAAGGTTTAGATGTACTTAGAAATAAATCTAATGGACAATGGATTACGTTTAATGAT
AsnLysGly LeuAspValLeuArgAsnLysSerAsnGlyGlnTrpIleThrPheAsnAsp
```

FIG. 2a-2

```
           910        920        930        940        950        960
     TATAAAAGAGAGATGACTATTCAAGTATTAGATATACTCGCTCTTTTGCCAGTTATGAT
     TyrLysArgGluMetThrIleGlnValLeuAspIleLeuAlaLeuPheAlaSerTyrAsp
           970        980        990       1000       1010       1020
     CCACGTCGATACCCTGCGGACAAAATAGATAATACGAAACTATCAAAAACAGAATTTACA
     ProArgArgTyrProAlaAspLysIleAspAsnThrLysLeuSerLysThrGluPheThr
          1030       1040       1050       1060       1070       1080
     AGAGAGATTTATACAGCTTTAGTAGAATCTCCTTCTAGTAAATCTATAGCAGCACTGGAG
     ArgGluIleTyrThrAlaLeuValGluSerProSerSerLysSerIleAlaAlaLeuGlu
          1090       1100       1110       1120       1130       1140
     GCAGCACTTACACGAGATGTTCATTTATTCACTTGGCTAAAGAGAGTAGATTTCTGGACC
     AlaAlaLeuThrArgAspValHisLeuPheThrTrpLeuLysArgValAspPheTrpThr
          1150       1160       1170       1180       1190       1200
     AATACTATATATCAAGATTTAAGATTTTTATCTGCCAATAAAATTGGGTTTTCATATACA
     AsnThrIleTyrGlnAspLeuArgPheLeuSerAlaAsnLysIleGlyPheSerTyrThr
          1210       1220       1230       1240       1250       1260
     AATTCTTCTGCAATGCAAGAAAGTGGAATTTATGGAAGTTCTGGTTTTGGTTCAAATCTT
     AsnSerSerAlaMetGlnGluSerGlyIleTyrGlySerSerGlyPheGlySerAsnLeu
          1270       1280       1290       1300       1310       1320
     ACTCATCAAATTCAACTTAATTCTAATGTTTATAAAACTTCTATCACAGATACTAGCTCC
     ThrHisGlnIleGlnLeuAsnSerAsnValTyrLysThrSerIleThrAspThrSerSer
          1330       1340       1350       1360       1370       1380
     CCCTCTAATGGAGTTACAAAAATGGATTTCTACAAAATTGATGGTACTCTTGCCTCTTAT
     ProSerAsnArgValThrLysMetAspPheTyrLysIleAspGlyThrLeuAlaSerTyr
          1390       1400       1410       1420       1430       1440
     AATTCAAATATAACACCAACTCCTGAAGGTTTAAGGACCACATTTTTTGGATTTTCAACA
     AsnSerAsnIleThrProThrProGluGlyLeuArgThrThrPhePheGlyPheSerThr
          1450       1460       1470       1480       1490       1500
     AATGAGAACACACCTAATCAACCAACTGTAAATGATTATACGCATATTTTAAGCTATATA
     AsnGluAsnThrProAsnGlnProThrValAsnAspTyrThrHisIleLeuSerTyrIle
          1510       1520       1530       1540       1550       1560
     AAAACTGATGTTATAGATTATAACAGTAACAGGGTTTCATTGCTTGGACACATAAGATT
     LysThrAspValIleAspTyrAsnSerAsnArgValSerPheAlaTrpThrHisLysIle
          1570       1580       1590       1600       1610       1620
     GTTGACCCTAATAATCAAATATACACAGATGCTATCACACAAGTTCCGGCCGTAAAATCT
     ValAspProAsnAsnGlnIleTyrThrAspAlaIleThrGlnValProAlaValLysSer
          1630       1640       1650       1660       1670       1680
     AACTTCTTGAATGCAACAGCTAAAGTAATCAAGGGACCTGGTCATACAGGGGGGGATCTA
     AsnPheLeuAsnAlaThrAlaLysValIleLysGlyProGlyHisThrGlyGlyAspLeu
          1690       1700       1710       1720       1730       1740
     GTTGCTCTTACAAGCAATGGTACTCTATCAGGCAGAATGGAGATTCAATGTAAAACAAGT
     ValAlaLeuThrSerAsnGlyThrLeuSerGlyArgMetGluIleGlnCysLysThrSer
          1750       1760       1770       1780       1790       1800
     ATTTTTAATGATCCTACAAGAAGTTACGGATTACGCATACGTTATGCTGCAAATAGTCCA
     IlePheAsnAspProThrArgSerTyrGlyLeuArgIleArgTyrAlaAlaAsnSerPro
```

FIG. 2a-3

```
       1810      1820      1830      1840      1850      1860
ATTGTATTGAATGTATCATATGTATTACAAGGAGTTTCTAGAGGAACAACGATTAGTACA
IleValLeuAsnValSerTyrValLeuGlnGlyValSerArgGlyThrThrIleSerThr
       1870      1880      1890      1900      1910      1920
GAATCTACGTTTTCAAGACCTAATAATATAATACCTACAGATTTAAAATATGAAGAGTTT
GluSerThrPheSerArgProAsnAsnIleIleProThrAspLeuLysTyrGluGluPhe
       1930      1940      1950      1960      1970      1980
AGATACAAAGATCCTTTTGATGCAATTGTACCGATGAGATTATCTTCTAATCAACTGATA
ArgTyrLysAspProPheAspAlaIleValProMetArgLeuSerSerAsnGlnLeuIle
       1990      2000      2010      2020      2030      2040
ACTATAGCTATTCAACCATTAAACATGACTTCAAATAATCAAGTGATTATTGACAGAATC
ThrIleAlaIleGlnProLeuAsnMetThrSerAsnAsnGlnValIleIleAspArgIle
       2050      2060      2070      2080      2090      2100
GAAATTATTCCAATCACTCAATCTGTATTAGATGAGACAGAGAACCAAAATTTAGAATCA
GluIleIleProIleThrGlnSerValLeuAspGluThrGluAsnGlnAsnLeuGluSer
       2110      2120      2130      2140      2150      2160
GAACGAGAAGTTGTGAATGCACTGTTTACAAATGACGCAAAGATGCATTAAACATTGGA
GluArgGluValValAsnAlaLeuPheThrAsnAspAlaLysAspAlaLeuAsnIleGly
       2170      2180      2190      2200      2210      2220
ACGACAGATTATGACATAGATCAAGCCGCAAATCTTGTGGAATGTATTTCTGAAGAATTA
ThrThrAspTyrAspIleAspGlnAlaAlaAsnLeuValGluCysIleSerGluGluLeu
       2230      2240      2250      2260      2270      2280
TATCCAAAAGAAAAAATGCTGTTATTAGATGAAGTTAAAAATGCGAAACAACTTAGTCAA
TyrProLysGluLysMetLeuLeuLeuAspGluValLysAsnAlaLysGlnLeuSerGln
       2290      2300      2310      2320      2330      2340
TCTCGAAATGTACTTCAAAACGGGGATTTTGAATCGGCTACGCTTGGTTGGACAACAAGT
SerArgAsnValLeuGlnAsnGlyAspPheGluSerAlaThrLeuGlyTrpThrThrSer
       2350      2360      2370      2380      2390      2400
GATAATATCACAATTCAAGAAGATGATCCTATTTTTAAAGGGCATTACCTTCATATGTCT
AspAsnIleThrIleGlnGluAspAspProIlePheLysGlyHisTyrLeuHisMetSer
       2410      2420      2430      2440      2450      2460
GGGGCGAGAGACATTGATGGTACGATATTTCCGACCTATATATTCCAAAAAATTGATGAA
GlyAlaArgAspIleAspGlyThrIlePheProThrTyrIlePheGlnLysIleAspGlu
       2470      2480      2490      2500      2510      2520
TCAAAATTAAAACCGTATACACGTTACCTAGTAAGGGGATTTGTAGGAAGTAGTAAAGAT
SerLysLeuLysProTyrThrArgTyrLeuValArgGlyPheValGlySerSerLysAsp
       2530      2540      2550      2560      2570      2580
GTAGAACTAGTGGTTTCACGCTATGGGGAAGAAATTGATGCCATCATGAATGTTCCAGCT
ValGluLeuValValSerArgTyrGlyGluGluIleAspAlaIleMetAsnValProAla
       2590      2600      2610      2620      2630      2640
GATTTAAACTATCTGTATCCTTCTACCTTTGATTGTGAAGGGTCTAATCGTTGTGAGACG
AspLeuAsnTyrLeuTyrProSerThrPheAspCysGluGlySerAsnArgCysGluThr
       2650      2660      2670      2680      2690      2700
TCCGCTGTGCCGGCTAACATTGGGAACACTTCTGATATGTTGTATTCATGCCAATATGAT
SerAlaValProAlaAsnIleGlyAsnThrSerAspMetLeuTyrSerCysGlnTyrAsp
       2710      2720      2730      2740      2750      2760
ACAGGGAAAAAGCATGTCGTATGTCAGGATTCCCATCAATTTAGTTTCACTATTGATACA
ThrGlyLysLysHisValValCysGlnAspSerHisGlnPheSerPheThrIleAspThr
```

FIG. 2a-4

```
        2770       2780       2790       2800       2810       2820
GGGGCATTAGATACAAATGAAAATATAGGGGTTTGGGTCATGTTTAAAATATCTTCTCCA
GlyAlaLeuAspThrAsnGluAsnIleGlyValTrpValMetPheLysIleSerSerPro
        2830       2840       2850       2860       2870       2880
GATGGATACGCATCATTAGATAATTTAGAAGTAATTGAAGAAGGGCCAATAGATGGGGAA
AspGlyTyrAlaSerLeuAspAsnLeuGluValIleGluGluGlyProIleAspGlyGlu
        2890       2900       2910       2920       2930       2940
GCACTGTCACGCGTGAAACACATGGAGAAGAAATGGAACGATCAAATGGAAGCAAAACGT
AlaLeuSerArgValLysHisMetGluLysLysTrpAsnAspGlnMetGluAlaLysArg
        2950       2960       2970       2980       2990       3000
TCGGAAACACAACAAGCATATGATGTAGCGAAACAAGCCATTGATGCTTTATTCACAAAT
SerGluThrGlnGlnAlaTyrAspValAlaLysGlnAlaIleAspAlaLeuPheThrAsn
        3010       3020       3030       3040       3050       3060
GTACAAGATGAGGCTTTACAGTTTGATACGACACTCGCTCAAATTCAGTACGCTGAGTAT
ValGlnAspGluAlaLeuGlnPheAspThrThrLeuAlaGlnIleGlnTyrAlaGluTyr
        3070       3080       3090       3100       3110       3120
TTGGTACAATCGATTCCATATGTGTACAATGATTGGTTGTCAGATGTTCCAGGTATGAAT
LeuValGlnSerIleProTyrValTyrAsnAspTrpLeuSerAspValProGlyMetAsn
        3130       3140       3150       3160       3170       3180
TATGATATCTATGTAGAGTTGGATGCACGAGTGGCACAAGCGCGTTATTTGTATGATACA
TyrAspIleTyrValGluLeuAspAlaArgValAlaGlnAlaArgTyrLeuTyrAspThr
        3190       3200       3210       3220       3230       3240
AGAAATATTATTAAAAATGGTGATTTTACACAAGGGGTAATGGGGTGGCATGTAACTGGA
ArgAsnIleIleLysAsnGlyAspPheThrGlnGlyValMetGlyTrpHisValThrGly
        3250       3260       3270       3280       3290       3300
AATGCAGACGTACAACAAATAGATGGTGTTTCTGTATTGGTTCTATCTAATTGGAGTGCT
AsnAlaAspValGlnGlnIleAspGlyValSerValLeuValLeuSerAsnTrpSerAla
        3310       3320       3330       3340       3350       3360
GGCGTATCTCAAAATGTCCATCTCCAACATAATCATGGGTATGTCTTACGTGTTATTGCC
GlyValSerGlnAsnValHisLeuGlnHisAsnHisGlyTyrValLeuArgValIleAla
        3370       3380       3390       3400       3410       3420
AAAAAAGAAGGACCTGGAAATGGGTATGTCACGCTTATGGATTGTGAGGAGAATCAAGAA
LysLysGluGlyProGlyAsnGlyTyrValThrLeuMetAspCysGluGluAsnGlnGlu
        3430       3440       3450       3460       3470       3480
AAATTGACGTTTACGTCTTGTGAAGAAGGATATATTACGAAGACAGTAGATGTATTCCCA
LysLeuThrPheThrSerCysGluGluGlyTyrIleThrLysThrValAspValPhePro
        3490       3500       3510       3520       3530       3540
GATACAGATCGTGTACGAATTGAGATAGGCGAAACCGAAGGTTCGTTTTATATCGAAAGC
AspThrAspArgValArgIleGluIleGlyGluThrGluGlySerPheTyrIleGluSer
        3550       3560       3570       3580       3590       3600
ATTGAATTAATTTGCATGAACGAGTGATTAATAAAAAATAACTAAAGCTTTAAAAACCAT
IleGluLeuIleCysMetAsnGlu***
        3610       3620       3630       3640       3650       3660
GGAGAAAGTTTTCTCCATGGTTTTTAATTTCTGCATTTATTAATTCTGGTACAAAAAATA
        3670       3680         0          0          0          0
TATAGAAAACATAAAAAATAGATA
```

FIG. 2b

```
         10         20         30         40         50         60
MNSGYPLAND LQGSMKNTNY KDWLAMCENN QQYGVNPAAI NSSSVSTALK VAGAILKFVN 70         80         90        100        110        120
PPAGTVLTVL SAVLPILWPT NTPTPERVWN DFMTNTGNLI DQTVTAYVRT DANAKMTVVK 130        140        150        160        170        180
DYLDQYTTKF NTWKREPNNQ SYRTAVITQF NLTSAKLRET AVYFSNLVGY ELLLLPIYAQ 190        200        210        220        230        240
VANFNLLLIR DGLINAQEWS LARSAGDQLY NTMVQYTKEY IAHSITWYNK GLDVLRNKSN 250        260        270        280        290        300
GQWITFNDYK REMTIQVLDI LALFASYDPR RYPADKIDNT KLSKTEFTRE IYTALVESPS 310        320        330        340        350        360
SKSIAALEAA LTRDVHLFTW LKRVDFWTNT IYQDLRFLSA NKIGFSYTNS SAMQESGIYG 370        380        390        400        410        420
SSGFGSNLTH QIQLNSNVYK TSITDTSSPS NRVTKMDFYK IDGTLASYNS NITPTPEGLR 430        440        450        460        470        480
TTFFGFSTNE NTPNQPTVND YTHILSYIKT DVIDYNSNRV SFAWTHKIVD PNNQIYTDAI 490        500        510        520        530        540
TQVPAVKSNF LNATAKVIKG PGHTGGDLVA LTSNGTLSGR MEIQCKTSIF NDPTRSYGLR 550        560        570        580        590        600
IRYAANSPIV LNVSYVLQGV SRGTTISTES TFSRPNNIIP TDLKYEEFRY KDPFDAIVPM 610        620        630        640        650        660
RLSSNQLITI AIQPLNMTSN NQVIIDRIEI IPITQSVLDE TENQNLESER EVVNALFTND 670        680        690        700        710        720
AKDALNIGTT DYDIDQAANL VECISEELYP KEKMLLLDEV KNAKQLSQSR NVLQNGDFES 730        740        750        760        770        780
ATLGWTTSDN ITIQEDDPIF KGHYLHMSGA RDIDGTIFPT YIFQKIDESK LKPYTRYLVR 790        800        810        820        830        840
GFVGSSKDVE LVVSRYGEEI DAIMNVPADL NYLYPSTFDC EGSNRCETSA VPANIGNTSD 850        860        870        880        890        900
MLYSCQYDTG KKHVVCQDSH QFSFTIDTGA LDTNENIGVW VMFKISSPDG YASLDNLEVI 910        920        930        940        950        960
EEGPIDGEAL SRVKHMEKKW NDQMEAKRSE TQQAYDVAKQ AIDALFTNVQ DEALQFDTTL 970        980        990       1000       1010       1020
AQIQYAEYLV QSIPYVYNDW LSDVPGMNYD IYVELDARVA QARYLYDTRN IIKNGDFTQG 1030       1040       1050       1060       1070       1080
VMGWHVTGNA DVQQIDGVSV LVLSNWSAGV SQNVHLQHNH GYVLRVIAKK EGPGNGYVTL 1090       1100       1110       1120       1130          0
MDCEENQEKL TFTSCEEGYI TKTVDVFPDT DRVRIEIGET EGSFYIESIE LICMNE
```

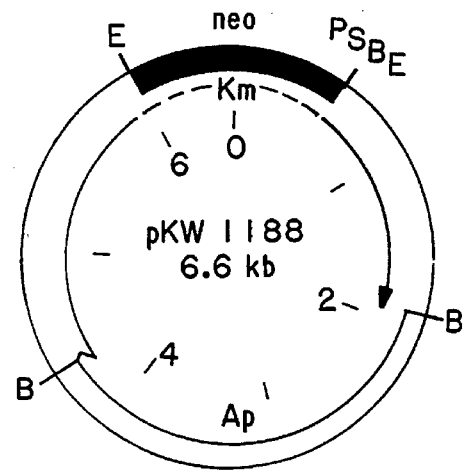
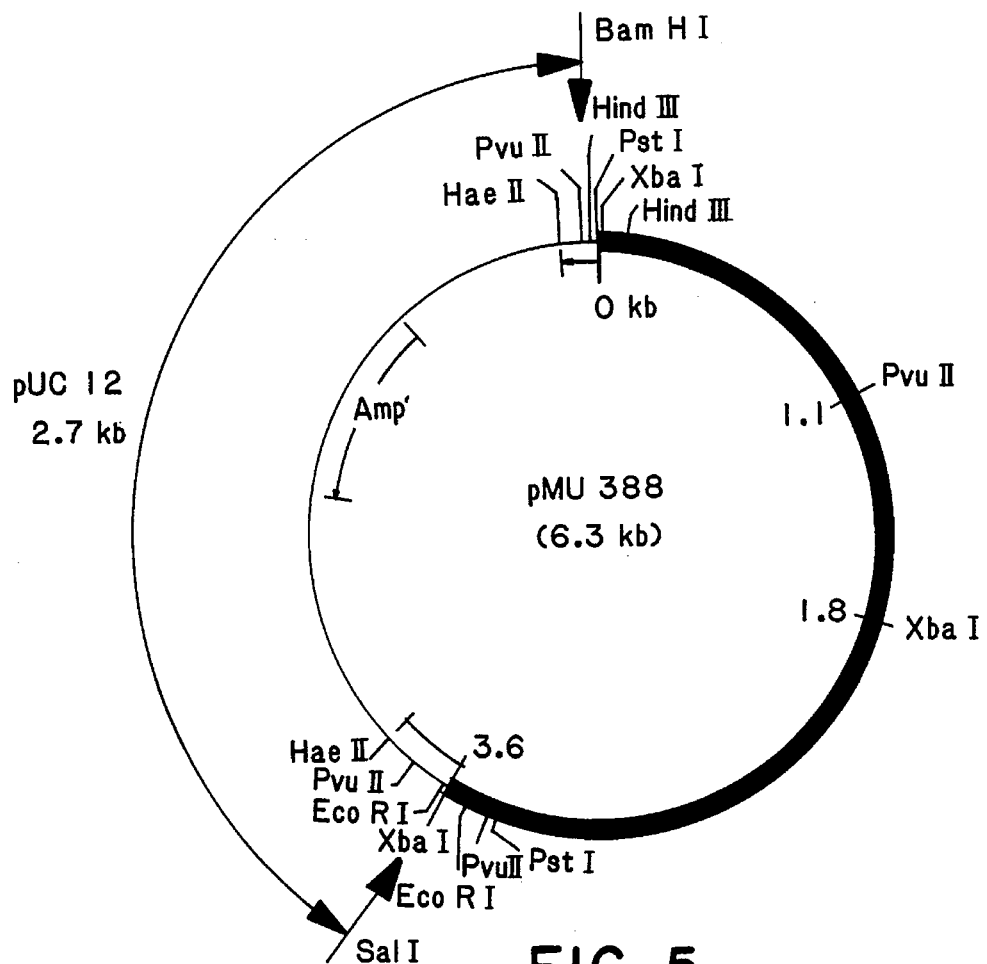
FIG. 5

HYBRID GENE INCORPORATING A DNA FRAGMENT CONTAINING A GENE CODING FOR AN INSECTICIDAL PROTEIN, PLASMIDS, TRANSFORMED CYANOBACTERIA EXPRESSING SUCH PROTEIN AND METHOD FOR USE AS A BIOCONTROL AGENT

The present invention relates to a hybrid gene incorporating a DNA fragment containing a gene coding for an insecticidal protein, more specifically a gene coding for an endotoxin active against Diptera. It also relates more particularly to recombinant vectors containing such gene or DNA fragment. It also relates to pro- and eukaryotic cells modified by these recombinant DNA vector.

The usefulness of *Bacillus thuringienses* endotoxins to control insect pests has been demonstrated over a wide range of crop and environmental pests.

*Bacillus thuringienses* var. israelensis has been used as a biological insecticide to combat mosquito and black fly larvae in swamps. These insects are a real problem for human health, especially in tropical areas (malaria, etc.)

Commercial formulations consist of a culture of *Bacillus Thuringiensis israelensis* bacterium in the sporulated stage consisting of spores and crystals. These crystals consist of proteins which have insect toxicity. These proteins act on the insect midguts when ingested by the larvae.

The main drawback of this approach is the fact that *Bacillus thuringiensis* bacterium is unstable in the environment (susceptible to U.V., washed away by intensive rains, etc.). Therefore one has to spray regularly which makes this method very expensive.

The special case worked out by this invention in order to ensure a better control of mosquitos concerns the use of transformed blue-green algae. Blue-green algae or Cyanobacteria are photosynthetic prokaryotic organisms. They constitute an important food base for mosquito larvae. A gene coding for a Bt endotoxin, active against mosquito, inserted in the genome of these organisms, represents an efficient way to combat larvae of mosquito. Since a number of mosquito species are important vectors of major human and animal diseases, and are living in regions difficult to control on a continuous base, a method which ensures a long-term destruction of this pest is attractive.

Indeed, the advantages of the use of toxins produced in a naturally occurring organism are multiple compared to the use of endotoxins in any other formulation form (e.g. sprays). The presence of the toxin in the food of the target insects guarantees direct uptake by the said insects.

Moreover, it assures a more stable availability of the toxin in the vicinity (self replicating, floating near the water surface . . .).

So the present invention deals with a chimeric gene capable of being expressed in Cyanobacteria cells comprising:

a) a DNA fragment comprising a promotor region which is effective for expression of a DNA fragment in a Cyanobacterium; and b) at least one DNA fragment coding for an insecticidally active protein produced by a Bacillus strain, or for an insecticidally active truncated form of the above protein or a protein having substantial sequence homology thereto.

Especially interesting are the chimeric genes wherein said DNA fragment b) codes for a protein produced by a strain of *Bacillus thuringiensis* var. israelensis.

Strains of the Gram-positive bacterium *Bacillus thuringiensis* (B.t.) produce intracellular protein crystals during the process of sporulation (Bulla et al. 1977). These crystal proteins, termed S-endotoxins, are toxic to a wide variety of Lepidoptera insects (Dulmage, 1979), some Diptera and Coleoptera. The endotoxins produced by different strains of B.t. may differ in their molecular structure and in their insect host range. In addition, one B.t. isolate may produce distinct types of crystal proteins.

*Bacillus thuringiensis* var. israelensis (Goldberg-Margalit, 1977), produces crystals that are highly toxic to larvae of mosquitos and black flies. In addition, the solubilized crystal proteins exhibit hemolytic activity and cytotoxicity towards mamalian cells (Thosmas & Ellar).

B.t. israelensis crystals contain three main polypeptides of 130, 65 and 28 kDa with distinct antigenic properties. Controversy still exists on which component is responsible for the potent mosquitocidal activity in B.t. israelensis crystals. Originally, both insect toxicity and homolytic activity were attributed to the 28 kDa protein. (Yamamoto, 1983; Armstrong, 1984). This was confirmed recently by molecular cloning and characterization of the B.t. israelensis gene encoding the 28 kDa crystal protein (Ward et al., 1984, 1986). On the other hand, using purified crystal protein fractions, Visser et al. showed that, while the 28 kDa protein is hemolytic, the specific mosquitocidal activité resides entirely in the protein of 130 kDa.

The present invention concerns preferentially the gene encoding the protein having mosquitocidal activity which is named B.t. 8 from *Bacillus thuringiensis* var. israelensis, encoding a 130 kDa crystal protein which structure is showed in FIG. 2, together with a truncated form of this protein.

Expression of the above cited proteins in Cyanobacteria needs to have methods for transformation of such organism.

A method has been described (McIntosh et al.) for targeting insertions of foreign DNA into the chromosome of the cyanobacterium Synechocystis 6803. This organism has a transformation system that enables it to take up exogenous DNA spontaneously. Donor DNA molecules were constructed by inserting a bacterial gene for kanamycin resistance into fragments of chromosomal DNA from the cyanobacterium. Recipient cells were transformed to kanamycin-resistance with a frequency as high as four transformants per thousand cells. Analysis of DNA from transformants by transfer hybridization showed that the kanamycin-resistance gene was inserted in the cyanobacterial chromosome. Integration occurred by replacement of chromosomal DNA with homologous DNA that contained the foreign insert.

The ability of some cyanobacterial species to take up exogenous DNA is central to the genetic modification. In many cyanobacteria, DNA added to the growth medium enters cells by a naturally-occurring mechanism, as shown by using DNA isolated from spontaneous antibiotic-resistant mutants to transfer the resistant phenotype to sensitive cells (Shestakov and Khyen, 1970; Astier and Espardellier, 1976; Stevens and Porter, 1980; Grigoreiva and Shestakov, 1982). This indicates that mutations in native cyanobacterial genes can be introduced into wild-type cells. Cyanobacteria can also take up foreign DNA, as demonstrated by transformation with recombinant plasmids consisting of bacterial antibiotic-resistance genes linked to native cyanobacterial plasmids (Buzby et al., 1983; Van de Hondel et al., 1980). In the cases, transformants were easily recovered on medium containing the appropriate antibiotics and were shown to harbor the recombinant plasmids. Another mechanism for DNA uptake, by conjugal transfer from *E. coli* cells, has been demonstrated recently with recombinant plasmids in a number of cyanobacterial species (Wolk et al., 1984). Whereas cyanobacterial plasmids could be useful for complementation studies, they are less valuable for modifying genes resident on the chromosome.

In bacteria, plasmids have been used to construct insertion mutations in chromosomal genes (Ruvkun and Ausubel, 1981). This is accomplished by inserting an antibiotic resistance gene into a chromosomal gene that has been cloned in the plasmid, then the plasmid is introduced into wild-type cells to allow the antibiotic resistance gene to move from plasmid to chromosome by homologous recombination, finally recombinants are selected by curing cells of the plasmid while continuing to select for antibiotic resistance. This procedure has not been used in cyanobacteria, in part because there is no efficient way to cure cyanobacteria of autonomously replicating plasmids (Tandenau de Marsac et al., 1982).

In an effort to develop a procedure for altering chromosomal genes in cyanobacteria, Williams and Szalay (1983) studied transformation in Synechococcus R2 using bacterial antibiotic resistance genes linked to fragments of Synechococcus R2 chromosomal DNA. It was found that the foreign DNA integrated efficiently into the Synechococcus R2 chromosome by homologous recombination and that, depending on the position of the resistance gene within the cyanobacterial DNA, mutant transformants could be constructed (Williams and Szalay, 1983; and unpublished results, JGKW). These characteristics of the Synechococcus R2 transformation system indicate that it should be possible to introduce modified genes into the chromosome of this organism.

Experiments reported by Williams and McIntosh show the Synchocystis 6803 is able to assimilate insertions of foreign DNA into its chromosome by homologous recombination, much as described in Synechococcus R2.

Based on these results, vector systems have been developed for transfer of foreign genes such as the B.t. gene into Cyanobacteria.

It is one object of the invention to provide novel chimeric genes coding for a mosquitocidal protein, preferentially protein of *Bacillus thuringiensis.*

Another object of the present invention is to provide novel hybrid plasmid vectors containing said chimeric genes said vectors allowing the integration of said chimeric genes in the genome or remaining extra-chromosomic.

A further object of the present invention is to provide Cyanobacteria transformed with said plasmids or said chimeric genes and a process for controlling mosquitos which comprises the use of said transformed Cyanobacteria.

Other objectives, features and advantages of the present invention will become apparent to those skilled in the art from the following description taken in conjunction with the accompanying drawings.

SUMMARY OF THE INVENTION

In accordance with the present invention, it is provided:

a chimeric gene capable of being expressed in Cyanobacteria cells comprising:

a) a DNA fragment comprising a promotor region which is effective for expression of a DNA fragment in a Cyanobacterium; and b) at least one DNA fragment coding for an insecticidally active protein produced by a Bacillus strain, or for an insecticidally active truncated form of the above protein or a protein having substantial sequence homology thereto.

Said chimeric genes include those where DNA fragment b) codes for a protein from Bacillus especially *Bacillus thuringiensis* or *Bacillus sphaericus* preferentially having anti-Diptera activity and especially those where DNA fragment b) codes for the protein named Bt8 corresponding to the structure shown in FIG. 2 and its truncated form with insecticidal activity.

Said chimeric genes include also those wherein DNA fragment b) is fused to a DNA fragment c) coding for a protein especially an enzyme capable of being expressed and permitting identification or selection of Cyanobacterium expressing DNA fragment b), especially those genes wherein the selectable or scorable marker is the neo gene.

It is known that amino-terminal fusions at the kanamycin resistance gene (neo gene) can generate fusion proteins that still confer kanamycin resistance in bacteria (Reiss et. al. EMBO J. 3, p. 3317, 1984).

Since kanamycin resistance is a most suitable selection marker both in bacteria and in Cyanobacteria, such gene fusions have promising applications. Indeed when using such NPTII fusion proteins to transform Cyanobacteria, a selection for kanamycin resistance allows direct selection for expression of the fusion product. Therefore, toxin gene fusions with neo may be used to transform Cyanobacteria and select for transformants expressing high levels of toxin, by selection for kanamycin resistance. This selection procedure is particularly useful in a "shotgun" approach whereby the fusion gene is inserted randomly behind Cyanobacterium DNA sequences before transformation. This allows to directly select for those constructs comprising the fusion gene behind a strong promoter inducing high levels of the fusion protein in Cyanobacteria.

Said DNA fragment b) is under the control of a promoter functional in cyanobacterium, it may be promotor region derived from the gene which is naturally expressed in said cyanobacteria such as the promoter sequence directing expression of the rubisco operon or a promoter region of another cyanobacterium or from a different organism such bacteria or phages, for example the lambdaPL promotor is functional in Synechocystis.

Said chimeric genes may be introduced in cyanobacteria by different method as described above especially by transformation using hybrid plasmids harboring the above chimeric genes.

Such plasmids may be used for integration of the chimeric gene within the genome of cyanobacteria, especially by homologous recombination. For such recombination hybrid plasmids comprise at least a chromosomic fragment of DNA of cyanobacteria and especially the chimeric gene is situated within the chromosomic fragment of DNA.

Said plasmid, without chromosomic fragment of Cyanobacterium DNA, may be used also as extra-chromosomic plasmids, for example with an origin of replication function in the Cyanobacterium.

Further, in accordance with the present invention there are provided: cyanobacterium which include in their cell genome or harbor a plasmid expressing the chimeric genes as described above.

Among the cyanobacteria the following may be used more particularly: Synechocystis, Anacystis.

But other species may also be used depending for example on the biotype: Synechococcus, Agmenellum, Aphanocapsa, Gloecapsa, Nostoc, Anabaena or Ffremyllia.

Still further in accordance with the present invention, there are provided insecticidal composition and methods using the transformed cyanobacterial and their progeny.

Said transformed cyanobacteria may be used as viable inocculum to settle the regions, especially the swamps and all stagnant waters which promote the growth of mosquito larvae.

But said cyanobacteria may also be used directly for the preparation of insecticidal formulation under any type of composition.

BRIEF DESCRIPTION OF THE DRAWINGS

FIG. 1: Restriction enzyme map of the XbaI insert in clone pMU388. Gene fragments contained in 2 deletion clones (Bt8 AccI and Bt8 NdeI) are also represented. Toxicity to mosquito larvae of E. coli cells containing the pUC12 with the different inserts is also indicated.

FIG. 2a: DNA sequence and deduced amino acid sequence of the 130 kd Bt israelensis toxin gene (Bt8). The putative ribosome binding site is underlined (position 145–149). 130 kd Bt israelensis toxin gene (Bt8). The putative ribosome binding site is underlined (position 145–149)

FIG. 2b: shows the amino-acid sequence of bt8.

FIG. 5: Shows the structure of pMU388 and pKW1188 synechocystis expression vector.

EXAMPLE 1

Figure 3:
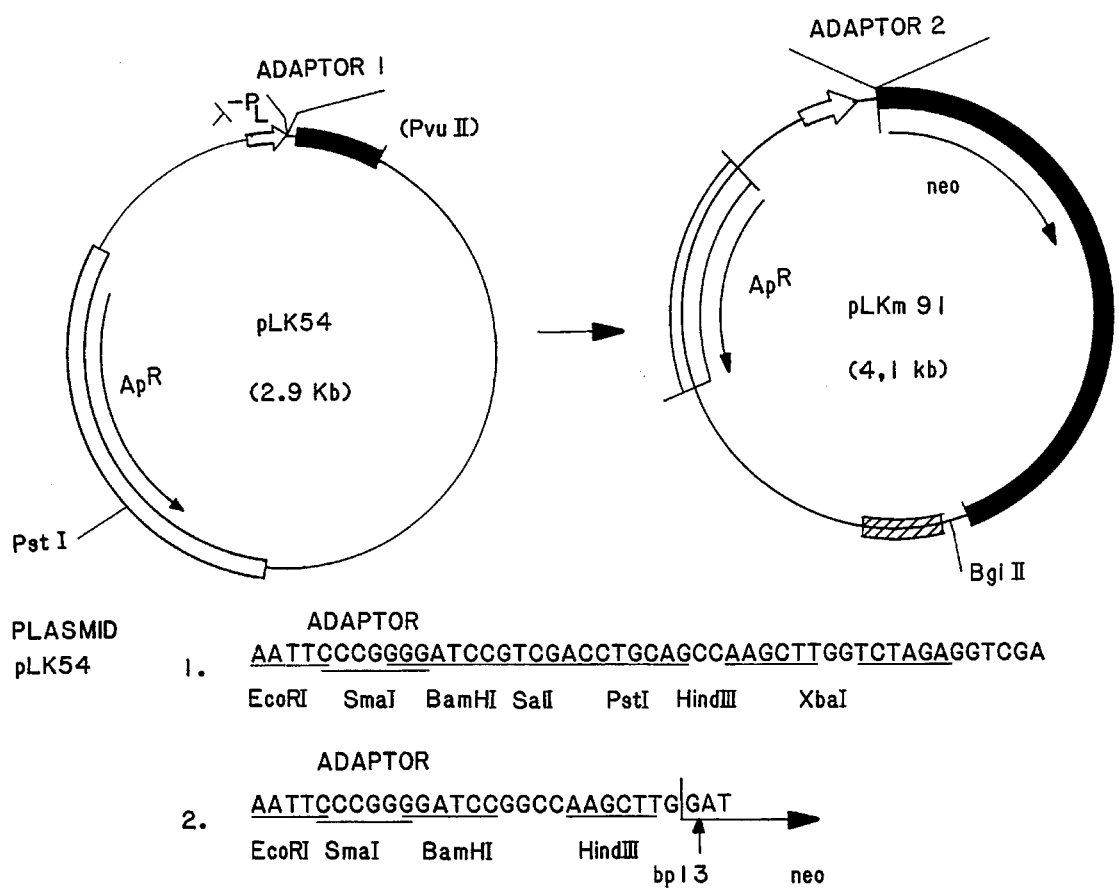
FIG. 3: Shows the strategy used for the positioning of the toxin gene behind the lambdaPL promotor in pLKm91.

Cloning of the *Bacillus thuringiensis* subsp. israelensis (Bti) toxin gene

A summary of the cloning manipulations is provided below.

The ±110 kb (±75 MDa) plasmid from *B.t.israelensis* 4Q272 (obtained from the Bacillus Genetic Stock Center, Columbia, Ohio) was isolated. The DNA was digested with appropriate restriction enzymes and ligated to linearized pUC12. Competent *E. coli* JM107 cells were transformed with the ligation mixtures. The recombinants were screened for the presence of toxin gene by RNA-DNA hybridization and subsequently for toxin production using an insect assay with mosquito larvae. One clone reacting positively in the hybridization assay and exhibiting high toxic activity to mosquito larvae was selected for further investigation and referred to as pMU388.

EXAMPLE 2

Expression in *E.coli* of a Bt.i 130 kDa crystal protein, exhibiting strong mosquitocidal activity

*E. coli* clone K514 (pMU388) is highly toxic to larvae of *Aedes aegypti* (Table 1), and therefore presumably harbors the gene for the mosquito-cidal crystal protein of *Bt.i*. The pMU388 plasmid contains the pUC12 with an Xba insert of ±3.6 kb. The restriction enzyme map of this Xba fragment is shown in FIG. 1.

Analysis of total cell extract of *E. coli* K514 (pMU388) in SDS-polyacrylamide gel (SDS-PAGE), reveals an intense protein band of ±130 kDa, the same apparent molecular weight as one of the major crystal proteins of *B.t.i*. This protein is not present in a control *E. coli* K514, containing the pUC12 vector without insert.

This ±130 kDa protein, termed Bt8, represents between 5 and 10% of the total protein content of the *E. coli* cells. It is present in the bacterial cells as a precipitate and, after lysis of the cells, can be selectively solubilized using a buffer with elakaline pH (9–10) containing a reducing reagent (DTT, ME).

The same conditions also allow efficient solubilization of original B.t.i-crystals. The solubilized, semi-purified Bt8 protein, has been used for toxicity assays on *A. aegypti* larvae.

The LC50 value for solubilized Bt8 protein was 100 ng/ml significantly higher than for native *B.t.i* crystals. However, for solubilized *B.t.i.* crystals a much higher L.C.50 was also recorded (50 ng/ml see Table 2). Since mosquito larvae are filter feeders this can be explained by less efficient absorption of soluble protein as compared to particles. Indeed toxicity of Bt8 protein could be enhanced by precipitating with citric acid (5 ng/ml) and unsolubilized Bt8 present in *E. coli* had an L.C.50 to the 5 ng/ml comparable of native Bti crystals (table 2).

Purified Bt8 protein solubilized in alkaline buffer was assayed for toxicity on insect cell lines "in vitro". While the 27 kDa toxin from Bti has been shown to cause complete lysis of *Aedes albopictus* cells at 50 ug/ml, Bt8 had no visible cytopathic effect even at 50 ug/ml. Therefore the Bt8 protein is clearly distinct from the 27 kDa Bti crystal protein in at least some of its functional properties.

Structural relationship between the cloned bt8 polypeptide and the 130 kDa protein present in Bti crystals, was confirmed by immunological data. In Western blotting the Bt8 protein reacts strongly with a rabbit antiserum raised against crystal proteins of *B.t.i.* strain 4Q2-72. In addition a rabbit antiserum raised against the purified Bt8 protein also reacts strongly with the 130 KDa protein of Bti crystals. Therefore we have cloned and expressed in *E. coli* a Bti gene encoding a protein with functional and structural properties analogous to those of a major B.t.i crystals protein.

EXAMPLE 3

Nucleotide Sequence of the toxin gene

Figure 4:
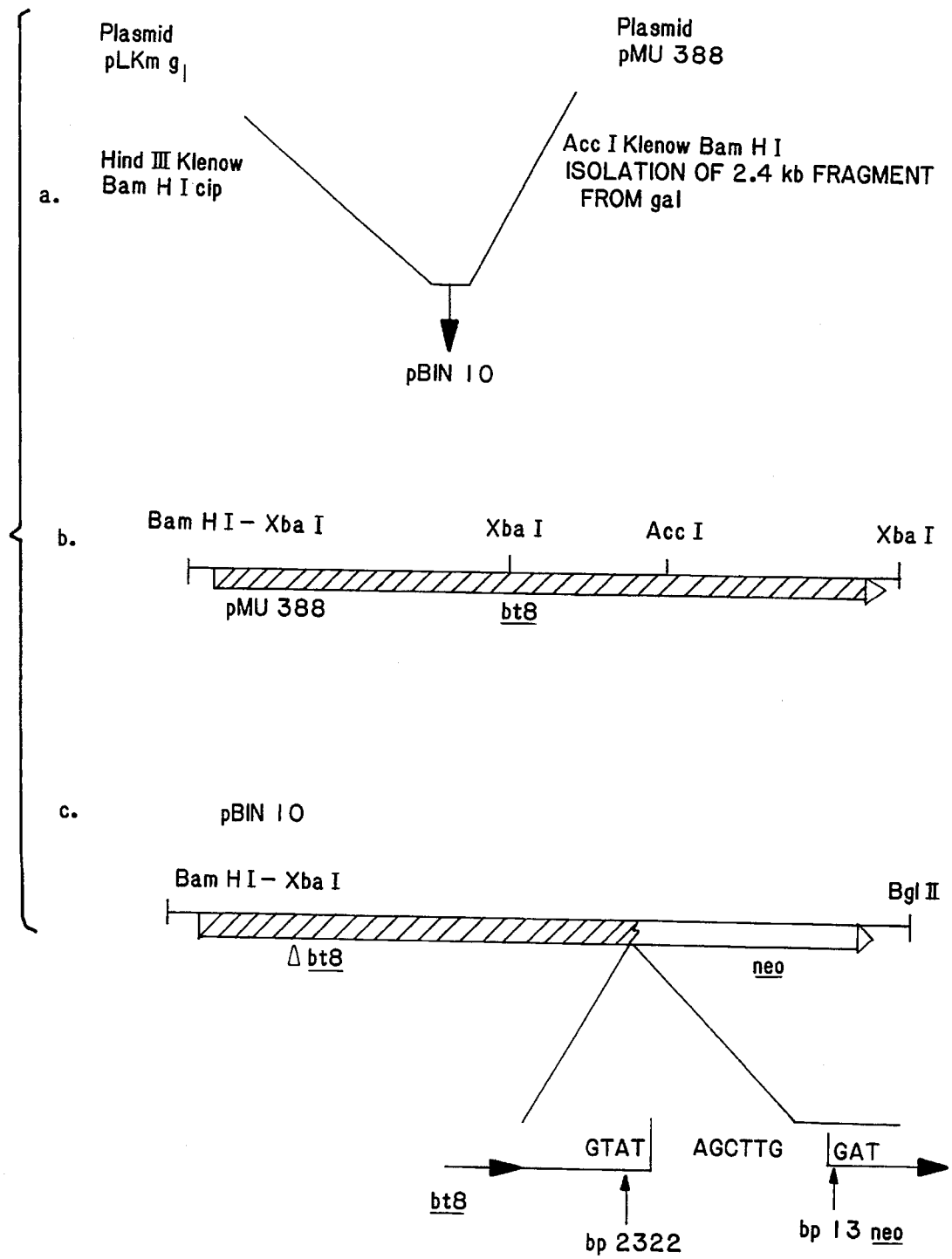
FIG. 4: Shows the construction of Bt8: neo from pMU388 and pLKm91.

The complete 3.6 kb insert of clone pMU388 was sequenced. The sequence (FIG. 4) reveals a single large open reading frame. Four clustered potential ATG start points for translation, which could give rise to a ±130 kDa polypeptide, were identified at bp positions 142, 157, 199 and 232 (FIG. 4). The ATG codon at position 157 was preceded by the consensus ribosome binding site GGAGG (bp 145–149). The reading frame starting at the ATG at bp position 157 and ending with a TGA stopcodon at position 3565 encodes a protein of 1136 amino acids, with a predicted molecular mass of 127000 Da, which agrees well with the estimated mass of Bt8 determined in SDS-PAGE. Bt8 protein produced by *E. coli* K514 (pMU388) was purified and an N-terminalamino acid sequence was determined by gas-phase sequencing. The obtained sequence Met-Asn-Xaa-Gly-Tyr-Pro-Leu-Ala-Asn-Asp-Leu was identical to the one deduced from the DNA sequence starting at ATG position 157 (FIG. 1) (Xaa indicates a residue which could not be unambiguously identified).

EXAMPLE 4

Identification of the toxin fragment essential for mosquitocidal activity

The 130 Da Lepodopteran specific B.t. endotoxins are protoxins, which after degradation by larval gut proteases yield smaller toxic polypeptides. We therefore investigated whether the 130 kDa mosquito specific Bt8 toxin would also generate smaller toxin fragments after protease treatment. Purified Bt8 protein was treated with either trypsin, chymotrypsin or with an extract containing proteolytic enzymes of A. aegypti larvae. After 1 h digestion at 37° C. the 130 kDa protein was completely degraded towards smaller polypeptide fragments. SDS-PAGE analysis revealed major protein bands of 48, 75 and 78 kD for trypsin, 65 and 68 kDa for chymotrypsin and 45 and 72 kDa for mosquito gut proteases. When tested in insect assays all these digested samples showed toxicity levels on mosquito larvae, comparable to intact 130 kDA Bt8 protein. A similar level of toxicity (LC50 value of 1 ug/ml) was also achieved by a 80 kDa fragment, a spontaneous degradation product from Bt8, generated after prolonged storage of this protein at 4° C. (probably by E. coli proteases in the Bt8 sample).

Prolonged treatment over a period of 12–18 h of Bt8 protein with mosquito proteases resulted in further degradation towards a major 45 kD polypeptide, which was essentially resistant to further proteolysis. This polypeptide sample however was not toxic any more to mosquito larvae. Similarly an 18-hour treatment with trypsin and chymotrypsin yielded major polypeptides of 48 and 50 kD respectively with a greatly reduced toxicity. The residual toxic activity still detected, probably is due to some nondigested 78 and 68 kD polypeptides still present in these preparations (FIG. 3). The present data indicate that the Bt8 toxin can be degraded by proteolytic enzymes, including mosquito midgut proteases, towards similar polypeptide fragments of 68–80 kDa, which have retained full mosquitocidal activity.

In order to localize the region essential for toxicity on the Bt8 molecule we constructed deletion mutants of clone K514 (pMu188) using existing restriction enzyme sites in the bt8 gene. Two 3' end deletion were generated: bt8 AccI containing a 5' fragment of bt8 up to the AccI site at bp position 2475 and bt NdeI ending at the NdeI site at bp position 1820. This clone produced proteins of the expected size of 90 kDa and 67 kDa respectively, as determined in Western blotting (data not shown). When tested in insect assays, the bt8 AccI clone exhibited mosquitocidal activity while the shorter bt8 NdeI clone was nontoxic. Thus the gene fragments encoding an active mosquitocidal polypeptide is localized in the N-terminal half of bt8 on a fragment defined by clone bt8 NdeI.

Materials and Methods for Examples 1 to 4

Purification of cloned B.t. toxin

The cell pellet from 1 liter saturated culture of E. coli (pMU388) was suspended in 100 ml of 50 mM Tris-HCl pH 7.9–50 mM EDTA-15% sucrose. The cell suspension was treated with lysozyme (100 ug/ml) for 30 min at 0° C. when sonicated on ice until the cells were lysed completely.

The bacterial debris was removed by centrifugation at 10,000 rpm, 4° C. for 20 min. The pellet was resuspended in 50 ml of 1 MNaCl-1% Triton X100-0.1 mM Phenylpethylsulfonyl fluoride (PMSF) and incubated at 0° C. for 30 min, then washed twice with 1 MNaCl-1% Triton×100 and once with phosphate buffered saline (PBS). The Bt8 protein, present in this "final pellet", was solubilized in 5 ml extraction buffer (0.1M $Na_2CO_3$ pH 9.5–0.2M thioglycolate) at 37° C. for 2 Hrs. The solubilized protein was dialysed against PBS. Purity of protein was judged by SDS-PAGE. The concentration of protein was determined by using protein assay reagent (Bio Rad) according to the directions of the supplier.

Proteolytic degradation of Bt8 protein

All the experiments were performed at 37° C. Purified Bt8 protein (1 mg/ml), solubilized in PBS-0.5% $NH_4HCl_3$, was digested with trypsin or chymotrypsin (Sigma) 20:1 w/w. In case of mosquito gut protease, purified Bt8 protein (1 mg/ml) in PBS-1M NaCl was digested with A aegypti gut protease 1:10 w/w.

Gut protease preparation: 50 third instar A. aegypti larvae gut 1 first instar M. sexta larvae mid gut were disrupted in 1 ml of 50 mM $Na_2XL_3$ pH 9.5–10 mM DTT in a sonic bath. The debris was removed by centrifugation at 10,000 rpm for 10 min. Protein concentration of the supernatant was estimated. The supernatant was stored in aliquots at 20° C.

Bioassay on mosquito larvae

A total of tested suspension 1 ml was placed in each wall of a 12 mm diameter microtiter plate. 10 third instar larvae of A. aegypti were added. Mortality was scored at 30° C. 24 hours. For acid precipitated samples, solubilized protein was precipitated by adding 1/10 vol. of 12% citric acid. Precipitated protein was pelleted by centrifugation and resuspended in distilled water.

Immunological assay

Antisera against B.t. protein(s) were obtained by subcutaneous injection of the protein(s) into New Zealand White rabbits. Specificity of antisera was confirmed by Western blotting using alkaline phosphatase conjugated anti-rabbit immunoglobulin (Sigma) to detect bound antibody according to the directions of the supplier.

Enzyme linked Immunosorbent Assay (ELISA) was performed to the method of Engval and Pesce.

Amino acid sequencing

Amino-terminal sequences of Bt8 protein were determined by using a gas-phase sequanator (Applied Biosystems Inc. USA) operated essentially according to Hewick et al.

DNA manipulations and computer analysis

Restriction endonuclease enzymes were used as described by the supplier (New England BioLabs, Inc.; and Bethesda Research Laboratories Inc.). Restriction mapping and subcloning were performed according to Maniatis et al. DNA sequences were determined by the Maxam and Gilbert method. Protein hydropathy was computed by the method of Kyte and Doolittle.

TABLE 1

The mosquitocidal activity of plasmid-harboring *E. coli* K514 to larvae of *A. aegypti*

| *E. coli* K514 clone | Mosquitocidal activity (dead/total) |
|---|---|
| pUC12 | 0/10 |
| pMU388 | 10/10 |
| bt8 Accl | 8/10 |
| bt8 NdeI | 0/10 | a) Cells from 4 ml culture at O.D.$_{600}$ 0.7 were harvested by centrifugation, and resuspended in 1 ml water.

TABLE 2

Toxicity of B.t.i and *B.t. berliner* crystal proteins on *M. Sexta* 1st instar larvae and *Aedes aegypti* 2nd instar larvae.

| B.t. toxin protein | *A. aegypti* LC50 (a) (ng/ml) | *M. sexta* LC50 (ng/cm$^2$) |
|---|---|---|
| B.t.i native crystals | 5 | >1500 |
| B.t.i solubilized crystals | 50 | >1500 |
| Bt8, solubilized (from *E. coli*) | 100 | >1500 |
| Bt8, precipitate (in *E. coli*) | 5 | n.t. |
| *B.t. berliner* native crystals | >100 | 80 |
| *B.t. berliner* solubilized crystals | >100 | 7.5 |
| Bt2, solubilized | >100 | 6 | a) LC50: Toxin concentration giving 50% mortality, determined after 24 h for *A. aegypti* and after 5 days for *M. sexta* larvae.
b) n.t.: not tested

EXAMPLE 5

Construction of the bt8: neo fusion gene

It was demonstrated in example 4 that a fragment of the coding sequence of gene bt8 (the 5' half of the gene up to bp position 2322 of the coding sequence, defined by an AccI site) encodes a toxic polypeptide.

This fragment was fused to the intact neo gene of Tn5 on pBR322 (Reiss et al., EMBO J. 1984).

a. Construction of pBIN10 comprising at bt8:neo fusion gene (FIG. 3)

pLKm91 has previously been described (Eur. patent appl. No. 85300291.1)

pMU388 was described in the thesis of C. ANGSUTHANASOMBAT pLKm91 DNA, treated with HindIII, the Klenow fragment of DNA polymerase (Klenow), BamHI and cip, was ligated to a 2.4 kb fragment obtained by treatment of pMU388 DNA with AcoI, Klenow and BamHI, and recovered from a preparative agarose gel. The recombinant clones were isolated by selection on Ampicillin (100 ug/ml) and screening for kanamycin (20 ug/ml) resistance.

b. Characteristics of the fusion protein expressed in *E. coli*

The fusion gene bt8:neo behind the PL promoter in plasmid construction pBIN10 was expressed in *E. coli*, to study the properties of the encoded fusion protein.

*E. coli* K12 H1 trp transformed with pBIN10 was analyzed in SDS-PAGE and in Western blotting. Coomassie staining of the complete bacterial extract in SDS-PAGE showed the presence of a new protein band having an apparent molecular weight corresponding to the expected size of the fusion protein (approximately 110 Kd). The protein could also be visualized in Western blotting using either anti-Bti crystal serum, anti-Bt8, or anti-NPTII serum. Again the positively reacting band showed the expected size of the fusion protein. The protein is quite stable in *E. coli* since almost no degradation products were detected (bands of lower M.W.).

The *E. Coli* clone K12ΔHΔ trp containing pBIN10 was indeed resistant to kanamycin. Bacteria were able to grow on 400 ug/ml Km (at 28° C.). NPTII activity of the fusion protein was evaluated using an NPTII assay as described (Reiss et al., Gene, 30, p. 217, 1984). A cell extract of the *E. coli* clone expressing the Bt8:NPTII protein was run on gel in nondenaturing conditions, in parallel with an extract from an *E. coli* clone producing the wild type NPTII. Cell extracts were prepared as follows.

The *E. coli* clones were grown during about 4 hours at 28° C. in 20 ml cultures (containing LB medium), centrifuged and resuspended in 1 ml TES buffer, sonicated twice at 50 watts in Labsonic 1510 and centrifuged for 30 minutes at 15 rmp; the supernatant was used in the experiment. The NPTII-specific activity of the proteins was determined by in situ phosphorylation of kanamycin, using 32p-ATP (Reiss et al., 1984, Gene 30, 217–223). The results indicated that the Bt8:NPTII protein exhibited specific NPTII activity.

*E. coli* clone K12ΔH1Δ trp (pBIN10) was analyzed for expression of functional toxin in an insect assay. Addition of the *E. coli* cells to the water killed *Aedes aegypti* larvae within 48 hours (Table 3). Control *E. coli* K12ΔH1Δ trp, not containing pBIN10, had no effect. Thus the Bt8:NPTII protein expresses both mosquito toxicity and NPTII enzyme activity.

Based on their results a vector system could be developed for transfer of foreign genes such as the B.t. genes into cyanobacteria.

EXAMPLE 6

Transformation of cyanobacteria a. The vector system for transformation of cyanobacteria Vectors for transformation of cyanobacteria are plasmids or linear DNA comprising bacterial antibiotic resistance genes linked to fragments of Synchocystis 6803 DNA. These plasmids will be referred to as "donor" DNA molecules", cyanobacterial cells mixed with donor DNA in transformation experiments are designated as "recipient cells". Each donor molecule consists of a fragment of Synechocystis 6803 cloned in an *E. coli* vector. The vector contains an ampicillin (Ap) resistance gene, (for selection in *E. coli*), whereas a kanamycin (Km) resistance gene (for selection of the transformed cyanobacteria) is inserted into the cyanobacterial DNA.

By way of example, we mention the donor plasmid pKW1188 (McIntosh et al.). It contains a fragment of Synechocystis 6803 chromosomal DNA cloned into *E. coli* pKW1159 and containing an inserted Km resistance gene from Tn903 (FIG. 5). Using this pKW1188 donor plasmid as a vector to transfer the Km resistance gene to Synechocystis, Km resistant cyanobacteria can be obtained at frequencies lower than 1 in 1000.

b. Method to transform Synechocystis

Synechocystis 6803 (Rippka et al., 1979) was obtained from the American Type Culture Collection. As determined by counting cells in a Petroff-Hauser chamber, an optical density ($A_{730}$) of 1.2 corresponds to about $10^8$ cells per ml. Cells were grown in BG-11 medium (Rippka et al., 1979) at 34° C. in a light flux of 1500 lux from warm white fluorescent tubes. Liquid cultures were perfused with air at 50–150 ml/min/100 ml culture volume. The air was moistened by bubbling through a solution of one percent $CuSO_4$ and sterilized by passage through two filters (Gelman no.12123 and no.4210). Under these conditions, a minimum of 8 h was required for the density of the culture to double. Solid medium was prepared by mixing an autoclaved solution of 3% Difco Bacto Agar with an equal volume of 2×BG-11 salts (Allen, 1968). *E. coli* HB101 (Bolivar and Backman, 1979) was used in all DNA constructions; it was cultivated in LB medium and cells were prepared for transformation by treatment with $CaCl_2$ (Maniatis and Fritsch, 1982); to select for transformants, kanamycin was used at 25 ug/ml, ampicillin at 50 ug/ml.

To prepare competent cells, an actively-grown culture (A730=0.3 to 2.0) of Synechocystis 6803 was diluted to A730=0.5 to 0.10 in fresh BG-11 medium and was grown overnight until A730 was between 0.2 and 0.4. The cells were harvested by centrifugation at room temperature, were suspended in BG-11 medium at A730=2.5 ($2\times10^8$ cells per ml), and were used immediately for transformation. Cells were mixed with donor DNA and were incubated in a glass tube under standard growth conditions, except that the cell suspension was not bubbled with air. We refer to this mixture of cells and DNA as a "transformation mixture". The DNA, in 10 mM Tris-HCl, pH 7.5, 0.1 mM EDTA, was added in a volume not greater than 2 percent of the volume of the cell suspension. After incubation for at least 2 h, 0.1 ml samples of the transformation mixture were spread on membrane filters (MF Membrane, 0.45 um, from Nuclepore, Pleassanton, Calif.) resting on agar medium in polystyrene petri plates. The plates were incubated for 18 to 20 h and the filters were transferred to agar medium containing the appropriate antibiotics (kanamycin at 5 ug per ml; ampicillin at 0.3 ug per ml). Colonies of transformed cells could be visualized within 4 days.

EXAMPLE 7

1. Creation of plasmid pBIK1188 (FIG. 5)
Recombinant plasmid pBIK1188 was created starting from plasmids pKW1188 (McIntosh et al., 1985) and pBIN10 (see Example 5), using the following experimental protocols:
  1. pKW1188 is:
    cut with HindIII and Klenow treated
    cut with SalI
so that part of the neo gene is cut out and a linear fragment of ±5.7 kb is obtained with one blunt end and one sticky end (from SalI)
  2. pBIN10 is:
    cut with SepI and SalI so that a linear fragment of ±4.2 kb, containing the bt8:neo gene behind the Lambda phage PL promoter, is obtained.
  3. Ligation of fragments obtained in 1) and 2) results in the recombinant plasmid pBIK1188. *E. Coli* K51: cells transformed with the ligation mixture are selected on Ap 100 ug/ml and Km 50 ug/ml, to select for clones containing plasmid pBIK1188.
    Plasmid p BIK1188 contains:
    A 5' fragment of the neo gene from Tn903 which was originally present on pKW1188 (up to the HindIII site). This is not a functional $Km^R$ gene any more.
    The bt8:neo fusion gene behind the PL promoter
    Synechocystis DNA fragments flanking the fusion gene
    The $Ap^R$ marker gene.
Thus plasmid pBIK1188 contains the bt8:neo gene behind a promotor which is functional in cyanobacteria (the PL promotor induces expression in cyanobacteria) (Friedberg and Seijffers, *Mol. Gen. Genet.* (1986) 203 p. 505–510). It can be used as donor plasmid to transfer and express this gene into cyanobacteria.

2. Selection of transformed cyanobacteria clones containing the bt8:neo gene;
Plasmid pBIK1188 can function as a "donor" plasmid to transfer the bt8:neo gene into the chromosomal DNA of Synechocystis. Since the $Km^R$ of the bt8:neo fusion is a functional $Km^R$ resistance gene, selection for $Km^R$ will allow to select for transformed clones of Synechocystis, containing this bt8:neo fusion gene.

Synechocystis 6803 cells were transformed with the "donor" plasmid and transformed clones were to be selected on medium containing 5 ug/ml Km. Several hundred transformed clones were obtained in one experiment. Two clones selected at random were used for further characterization: clone 20 and clone 43.

3. Characteristics of transformed cyanobacteria
  1. Southern blotting confirmed the presence of the bt8:neo gene in clones 20 and 43:
    Cyanobacterium clone 20 and clone 43 chromosomal DNA was purified and digested with BamHI or EcoRI restriction enzymes. Southern blotting of the digested DNA showed that the 1.8 kb XbaI fragment from 5' end of the bt8 toxin gene, used as probe, hybridized with a 3.4 kb EcoRI and with a 3.6 kb BamHI fragment of the cyanobacterium chromosomal DNA. This result indicates that the bt8:neo fusion gene did integrate into the chromosome of cyanobacterium clones 20 and 43.
  2. Expression of the recombinant protein Bt8:NPTII in clones 20 and 43 was analyzed using immunological assays. Western blotting showed that indeed these clones expressed the Bt8:NPTII fusion protein:
    Total cell lysate of the cyanobacterium clones was separated on SDS-PAGE, the protein were transferred onto nitrocellular paper and probed with either a rabbit anti Bt8 serum or a rabbit anti-NPTII serum. The results showed the presence in clones 20 and 43 of a new polypeptide with apparent mW of 110,000 Da which reacted with both anti-Bt8 and anti-NPTII antibodies. This protein was not detected in untransformed Synochocystis cells. Thus clones 20 and 43 express the Bt8:NPTII fusion protein.

EXAMPLE 8

Figure 6:
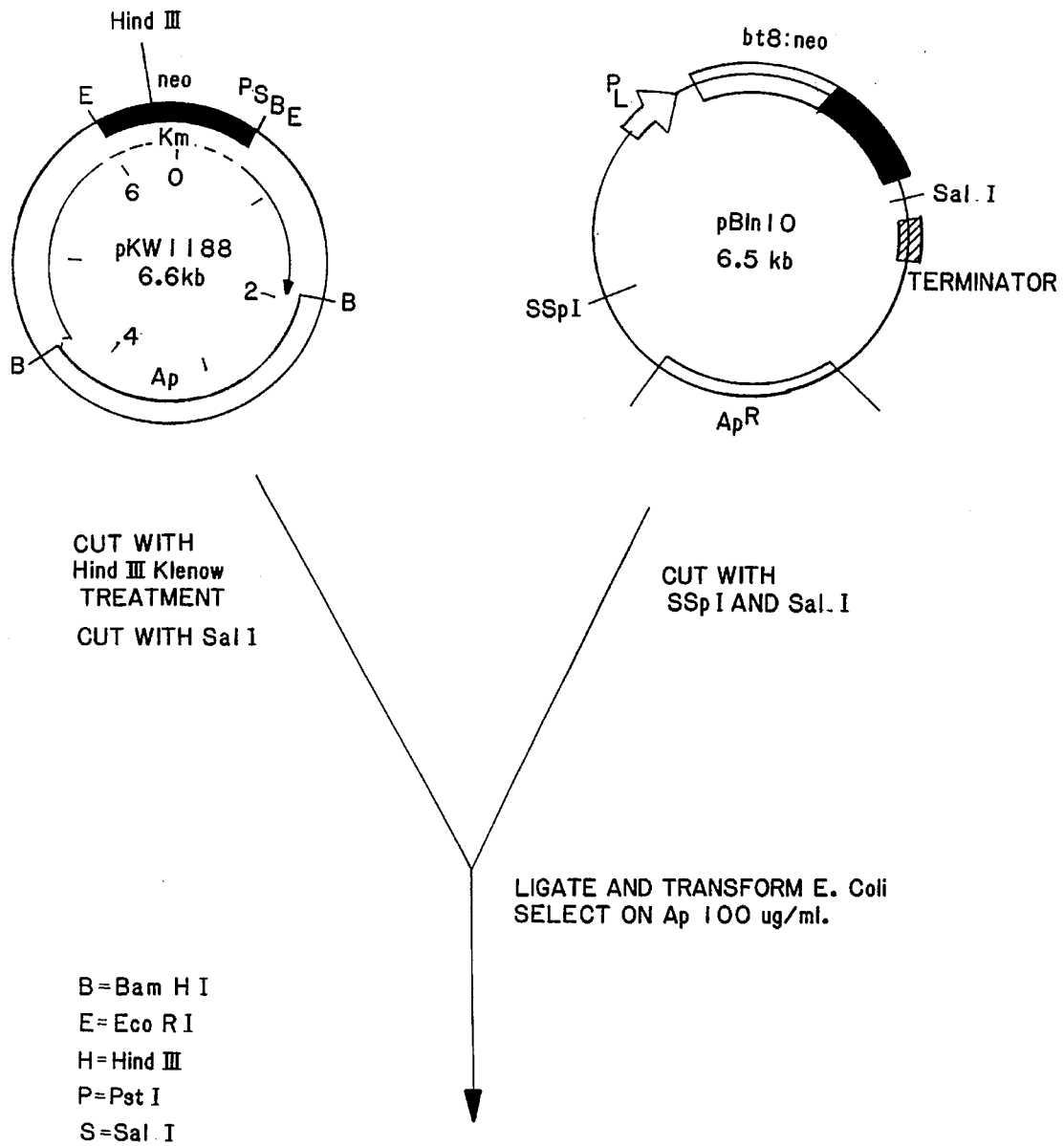
FIG. 6: Shows the construction of pB1K 1188.
Figure 7:
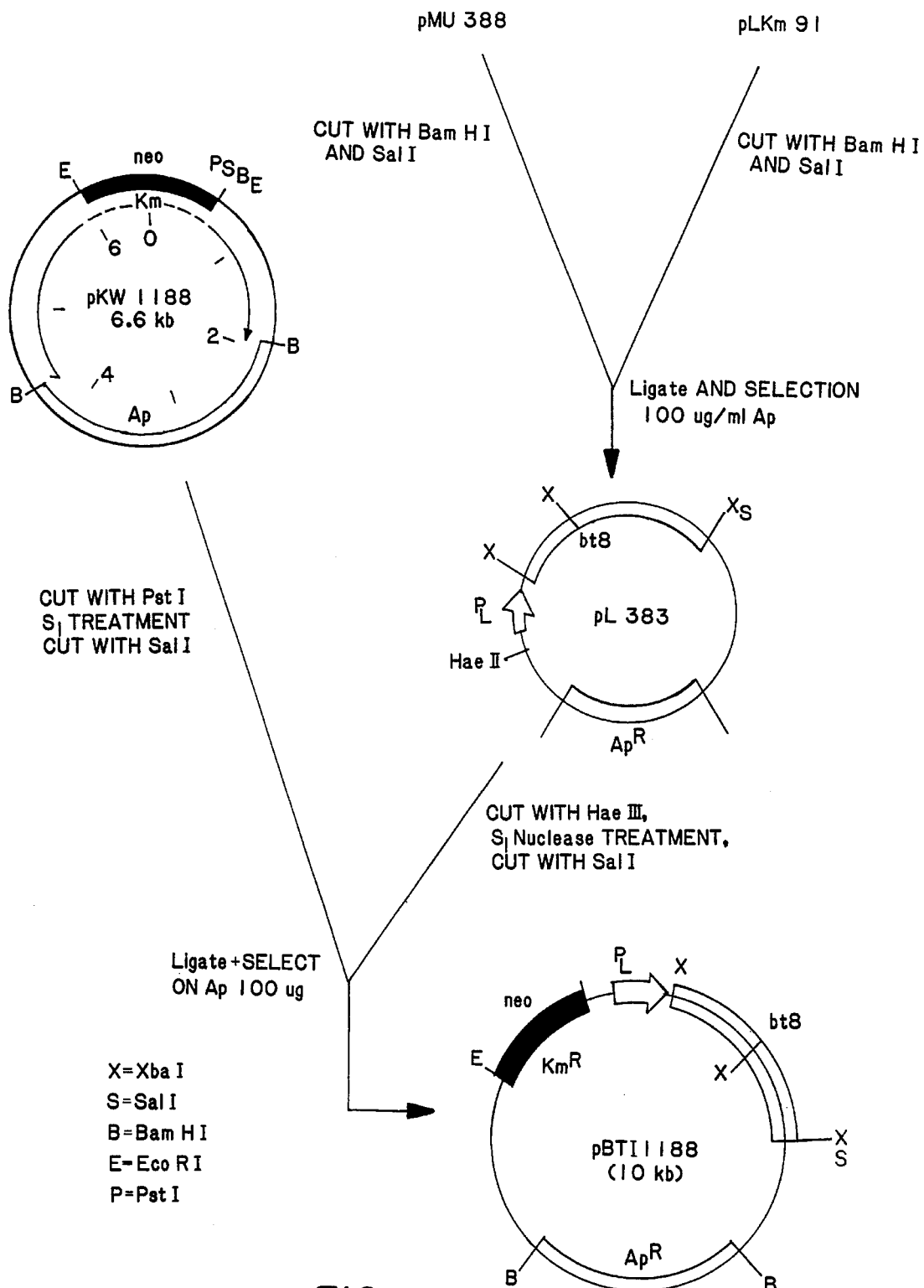
FIG. 7: Shows the construction of pBIT 1188.

1. Creation of plasmid pBTI1188 (FIG. 7)
To obtain pBTI1188, the complete tb8 toxin gene from plasmid pMU388 is placed behind the Lambda $P_L$ promotor and cloned into pKW1188, next to the $Km^R$ gene (FIG. 6). The intact $Km^R$ gene of pKW1188 is still present and can be used as a selection marker for screening transformants.

1.1 Construction of pL383 containing the intact bt8 gene behind the PL promoter
  1. pMU388:
    cut with BamHI and SalI
    a linear DNA fragment of ±3.6 kb with 2 sticky ends containing the bt8 gene is obtained.
  2. pbKm91:
    cut with BamHI and SalI
    a linear ±2.9 kb DNA fragment is obtained, comprising the PL promoter and $Ap^R$ gene.
  3. Ligation of the fragments obtained in 1. and 2. Ligation mixture is transformed in K514 *E. coli* and transformed clones are selected for $Ap^R$ (100 ug/ml).

1.2 Construction of pBTI1188:
1. p1383:
cut with HaeII (+S1 treatment) and SalI
a linear ±4 kb DNA fragment containing bt8 behind PL
2. pKW1188:
cut with PstI+S1 treatment and cut with SalI
a 6.6 kb linear vector fragment is obtained
3. Ligate the fragments obtained in 1. and 2. and select transformed E. coli on 100 ug/ml Ap.
Plasmid pBTI1188 contains:
the bt8 gene behind the PL promoter
a functional neo gene
flanking Synechocystis chromosomal DNA sequences
$Ap^R$ marker gene 2. Transformation of cyanobacteria with pBTI1188 and selection of transformed clones Plasmid pBTI1188 has been used as donor plasmid to transfer the bt8 into Synechocystis 6803 cells. Transformed 6803 clones were selected on medium containing 5 ug/ml of Km. Several hundreds of transformed colonies were obtained per 1 ug of DNA.

EXAMPLE 9

B.t. derived toxin genes are placed behind a strong promoter yielding high expression in cyanobacteria such as f.e., the Synechocystis 6803 promoter for the rubisco operon.

Figure 8:
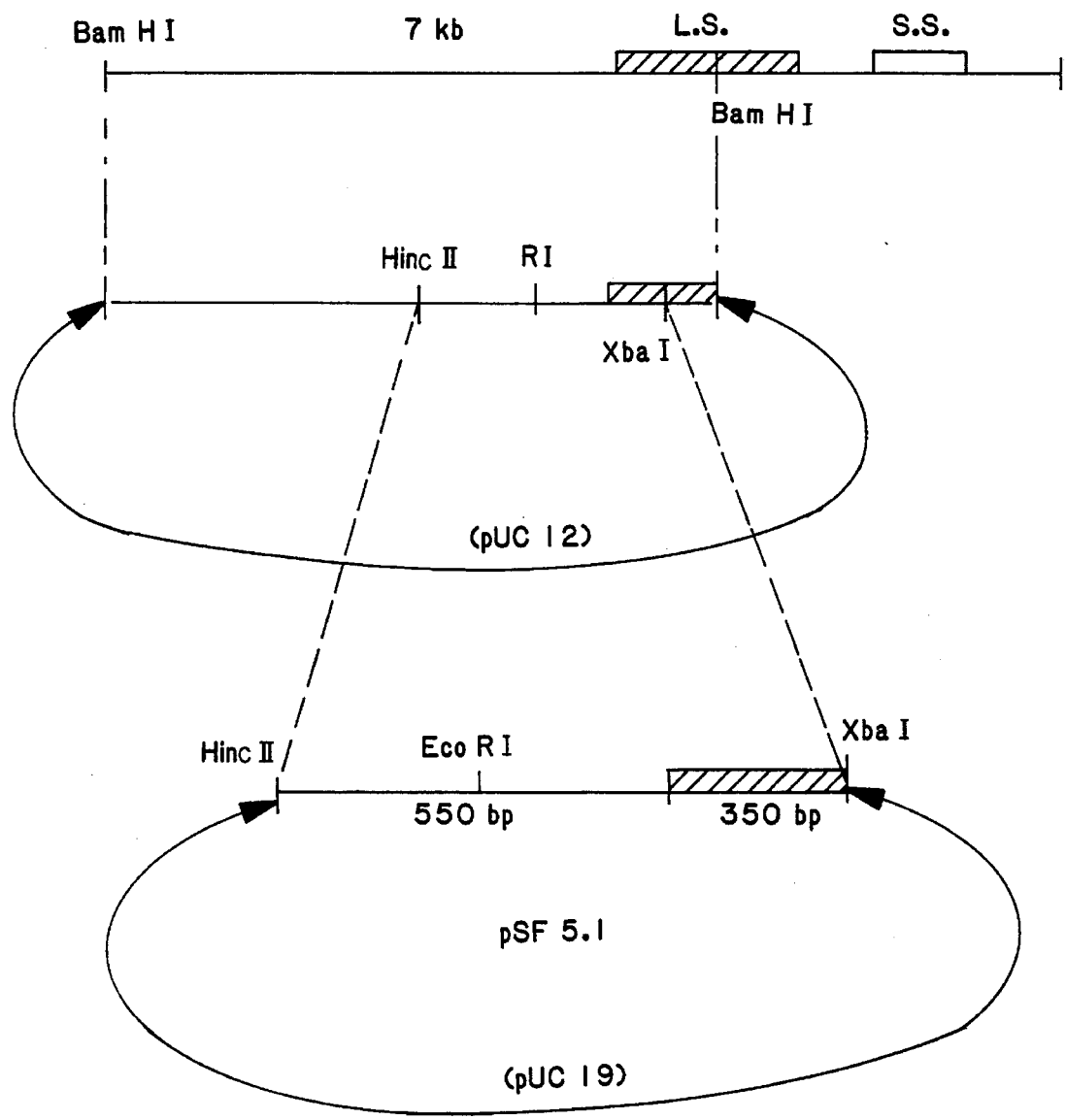
FIG. 8: Shows the isolation of a DNA fragment from Synechocystis 6803 comprising the promotor sequence directing expression of the rubisco operon.
Figure 9:
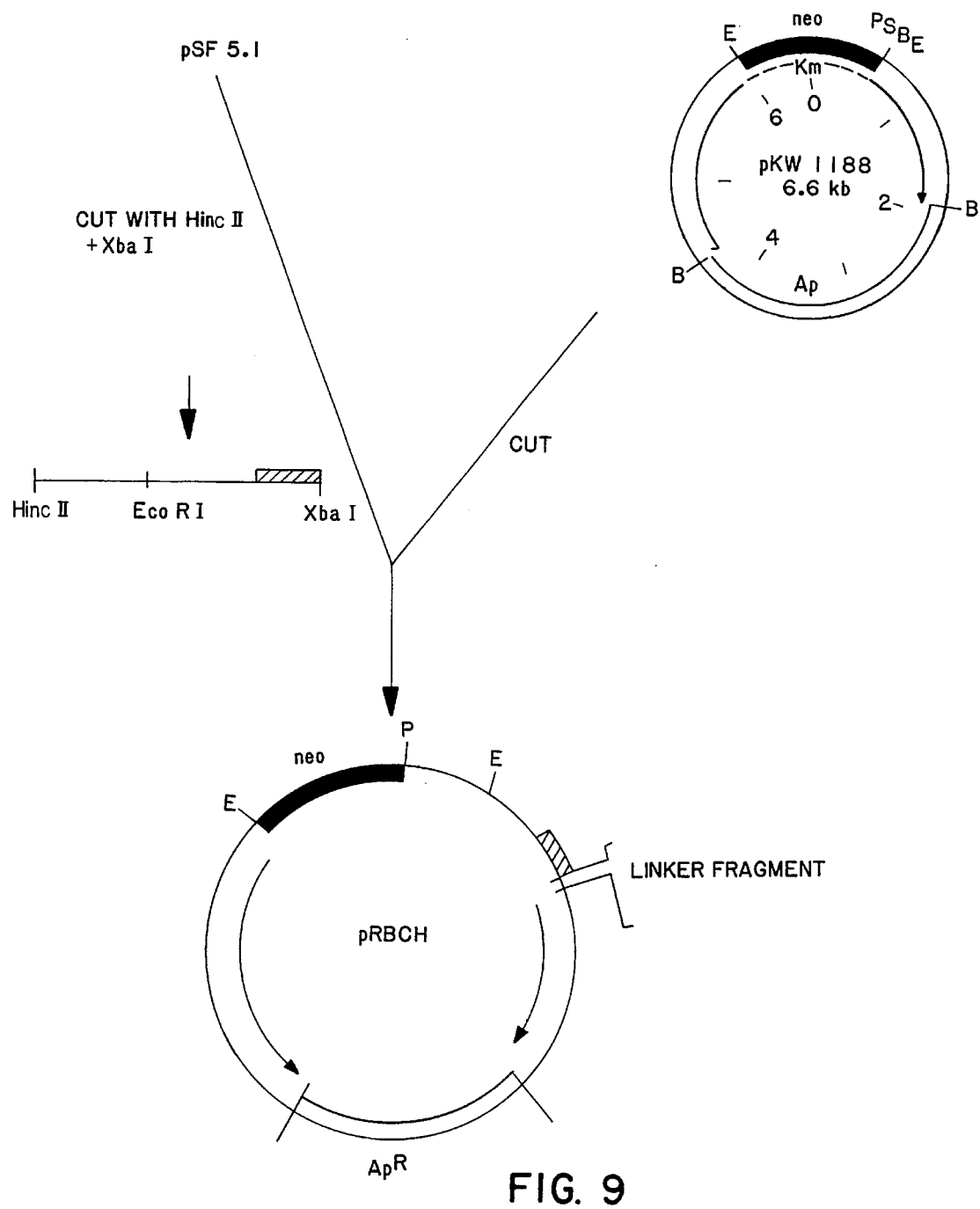
FIG. 9: Shows the construction of plasmid pRBC4

1. Creation of a vector comprising the B.t. genes behind the Synechocystis 6803 promoter for the rubisco operon:

The rubisco operon of Anabaena has been cloned and characterized (PNAS, 80, 1835–1839, 1983 and PNAS, 81, 5961–5965, 1984). Using part of this sequence as probe, a DNA fragment comprising, presumably, the promotor and part of the coding sequence of the large subunit of rubisco (L.S.) has been cloned from Synechocystis into E. coli (FIG. 5). From this ±7 kb BamHI fragment a ±900 bp HincII-XbaI fragment has been sub-cloned into pUC19, generating plasmid pSS 5.1 (FIG. 8). This fragment contains ±550 bp of 5' upstream sequence and ±350 bp of the L.S. coding region.

This fragment was recombined into expression vector pKW1188 to create a new plasmid called pRBC4 (FIG. 8). Just behind the coding sequence of L.S., a linker fragment containing a number of cloning sites, was inserted.

Therefore pRBC4 contains:

all elements present on pKW1188 a 5' upstream sequence of the Synechocystis L.S. gene, presumably comprising the promoter sequence for the rubisco operon part of the L.S. coding sequence a linker fragment containing suitable, restriction enzyme sites for cloning (XbaI, EcoRV, SalI, BamHI, EcoRI)

B.t. genes (bt8 and bt8:neo) have been inserted in the cloning site of pRBC4. The obtained recombinant plasmids were used to transform Synechocystis 6803 and to transfer the B.t. genes inserted behind a promoter fragment which induces high level expression of these genes.

TABLE 3

Mosquitocidal activity of E. coli clones harboring bt8 derived toxin genes (number of dead 2nd instar Aedes aegypti larvae).

| E. coli clone | No $10^8$ cells/ml | Toxin | Number of dead/viable larvae 20 h | 48 h |
|---|---|---|---|---|
| Control pUC12 | 7 | — | 0/10 | 0/10 |
|  | 28 |  | 0/10 | 0/10 |
| PMU388 | 7 | Bt8 | 4/10 | 6/10 |
|  | 28 |  | 10/10 | 10/10 |
| pLKm91 | 7 |  | 0/10 | 0/10 |
|  | 28 |  | 0/10 | 0/10 |
| PBIN10 | 7 | Bt8:NPTII | 3/10 | 9/10 |
|  | 28 |  | 3/10 | 9/20 |

The following strains have been deposited in the Deutsche Sammlung von Mikroorganismen (DSM):

E. coli K 514 harboring the plasmid pMU388

E. coli K12ΔHIΔtrp harboring the plasmid PIBN10.

PBIK 1188 (FIG. 6) has been deposited as IVI 10129 and PBIK 1188 (FIG. 7) has been deposited ad IVI 10130 on Mar. 4, 1987 under the Budapest Treaty with In Vitro International, Inc., 611 Hammonds Ferry Road, Linthicum, Md. 21090.

BIBLIOGRAPHY

The following documents have been cited in the specification:

Lee McIntosh et al. in Molecular Form and Function of the Plant Genome; Plenum Press, New York, 1985, pp. 335–346.

Thesis of Chanun Angsuthanasombat, Molecular cloning and expression of A δ-endotoxin gene of Bacillus Thuringiensis var. israelensis in Escherichia coli, Mahidol University, 1985, Bangkok—Thailand

We claim:

1. A plasmid p1BN10 harbored in E. coli K12ΔH1Δtrp having been deposited in DSM under the accession number 4020.

\* \* \* \* \*